United States Patent [19]

Daher et al.

[11] Patent Number: 5,122,385
[45] Date of Patent: Jun. 16, 1992

[54] METHOD FOR PRODUCING A SHINE COATING BY AQUEOUS SPRAYING AND FLASH DRYING

[75] Inventors: Lawrence J. Daher; Lonnie C. Sackman, both of Elkhart, Ind.

[73] Assignee: Miles Inc., Elkhart, Ind.

[21] Appl. No.: 787,734

[22] Filed: Nov. 4, 1991

Related U.S. Application Data

[63] Continuation of Ser. No. 386,950, Jul. 31, 1989, abandoned.

[51] Int. Cl.$^5$ ............................................. A61K 9/36
[52] U.S. Cl. ........................................ 427/3; 424/480; 427/212; 427/379
[58] Field of Search ............ 427/3, 212, 331, 385.5, 427/379; 424/463, 464, 474, 475, 480

[56] References Cited

U.S. PATENT DOCUMENTS

| | | | |
|---|---|---|---|
| 3,371,015 | 2/1968 | Sjogren et al. | 424/475 |
| 3,383,236 | 5/1968 | Brindamour et al. | 427/3 |
| 4,302,440 | 11/1981 | John et al. | 424/480 |
| 5,047,258 | 9/1991 | Belanger et al. | 427/3 |

FOREIGN PATENT DOCUMENTS

1444890  8/1976  United Kingdom ............ 427/3

OTHER PUBLICATIONS

FMC Corporation Manual AQUACOAT The Revolutionary Aqueous Coating System pages on 24 inch Acella-Cota settings (undated).

Primary Examiner—Michael Lusignan
Assistant Examiner—Terry J. Owens
Attorney, Agent, or Firm—M. G. Boguslaski

[57] ABSTRACT

A method for producing a tablet shine coating by either (a) alternately spray flooding the surfaces of tablets with a clear aqueous coating solution which is devoid of plasticizers, such as a solution consisting essentially of about 6% hydroxypropyl methylcellulose, about 0.06% sodium hexametaphosphate and about 0.006% lecithin by weight in water, and flash drying the tablets, or (b) alternately spray flooding the surfaces of coated tablets with water and flash drying the tablets.

3 Claims, No Drawings

METHOD FOR PRODUCING A SHINE COATING BY AQUEOUS SPRAYING AND FLASH DRYING

This is a continuation, of application Ser. No. 386,950, filed Jul. 31, 1989, now abandoned.

FIELD OF THE INVENTION

The invention relates to a method of producing a film coated tablet in general, to a method of producing a shine or gloss film coated tablet using aqueous solvents in particular and a coating composition for use in the method.

BACKGROUND OF THE INVENTION

Pharmaceutical tablets are traditionally given a finishing film coating that is designed to provide a gloss or shine to the final tablet in order to improve the appearance to the consumer. A commonly practiced method is to apply a thin layer of unpigmented coating on top of the usually pigmented color coat. While this method is generally successful when the final coating is applied with an organic solvent, there have been problems using aqueous based coatings. The result is often a low shine or dull appearance in contrast to tablets prepared with an organic solvent method.

FMC Corporation has produced a looseleaf manual on film coating entitled AQUACOAT The Revolutionary Aqueous Coating System available from FMC Corporation, Food and Pharmaceutical Products Division, 2000 Market Street, Philadelphia, Pa. 19103, which provides information on the use of a 24 inch Accela-Cota ® pan for color coating and gloss coating of several vitamin products Machine settings and formulations are given therein. The formulations and process described in this manual are typical for gloss coating, or shining, of pharmaceutical tablets when using aqueous based film coating solutions. The process described is a continuous coating process, i.e. a gloss coating solution is applied at a continuous rate. That rate is chosen to be consonant with the capability to continuously dry the tablet surfaces of the newly applied gloss coating solution. The gloss coating solution formulation provided is also typical and is based on the use of unpigmented hydroxypropyl methylcellulose, (HPMC), plasticized by liquid plasticizers, in an effort to achieve film clarity and flexibility.

Tablets coated by the method of this invention have an improved appearance over those made with the settings and formulations suggested in the FMC manual.

Vitamins coated by the method of this invention were shipped in interstate commerce Nov. 7, 1988, by MILES INC., 1127 Myrtle Street, Elkhart, Ind. 46514, under the trademark One-A-Day ® Maximum Formula.

This invention provides a method to produce a shine coating with aqueous coating solutions or with water; thereby avoiding both the problem of exposure of workers to organic solvents and the problem of disposal of the organic solvents.

SUMMARY OF THE INVENTION

The method of the invention may be used to provide a shine to a tablet which has been aqueous film coated by traditional methods, comprising the steps of:
a. intermittently spray flooding tablet surfaces with water; and
b. flash drying the flooded tablets.

The invention also provides a method of producing an aqueous shine coating, comprising the steps of:
a. intermittently spray flooding tablet surfaces with an aqueous solution of film material devoid of plasticizer; and
b. flash drying the flooded tablets.

The method preferably comprises the steps of:
a. intermittently spraying film coated tablets with water using spray rates of between about 200 grams per minute to about 600 grams per minute per spray gun for a period of time sufficient to flood the surface of the tablets while rotating the tablet pan at a rate of less than about 10 revolutions per minute and maintaining a tablet bed at temperatures between about 50 and 65 degrees Centigrade;
b. stopping the spraying while maintaining the tablet pan rotation and tablet bed temperature; and
c. drying the flooded tablets at an inlet temperature greater than about 90° Centigrade and a temperature drop between the inlet and exhaust air temperature of from about 30° to 70° Centigrade.

The methods preferably make use of these steps in a repeated manner using intermittent spray flooding and flash drying until the tablets have achieved acceptable shine characteristics.

Preferably the composition of the aqueous film coating solution is devoid of plasticizer. A particularly preferred aqueous clear coating solution is composed of about 6% hydroxypropyl methylcellulose and less than about 1% of a combination of sodium hexametaphosphate and lecithin, by weight, in water.

DESCRIPTION OF THE INVENTION

Film coated pharmaceutical tablets are often given a finishing coat to provide a desirable gloss or shine. Commonly this finishing coat is produced by applying a thin layer of unpigmented coating on top of the usually pigmented color coat. This approach seems to work well with organic solvent based coatings, but not nearly as well with aqueous based coatings Aqueous based coatings, when glossed, are dull, or at least have a low shine in comparison to tablets with organic based coatings. While aqueous film coating is desirable from an environmental standpoint, both for workers and for disposal, the consumer perception is that these tablets are "different" and perhaps of a lower quality than previous "shinier" tablets.

Previous shine coating methods (as described in the FMC manual cited earlier in the specification) have sought to balance the wetting and drying of the coating to assure that the tablet surface is dry while still allowing for the application of new layers of sprayed coating. This has been accomplished by balancing the spraying rate and the drying temperature to be sure that the coating solution is applied continuously at a rate of application that is exactly commensurate with the instantaneous drying rate. This balance is not optimum for film clarity and gloss.

In addition, previous shine coating methods attempt to achieve tablet surface gloss through the use of specifically formulated coating compositions and by applying a smooth coating layer. Earlier aqueous film coating processes attempted to achieve a smooth surface gloss by running the coating factor balance in the more wet rather than more dry area of moisture control and by using a cooler, rather than warmer, drying temperature range than was used for organic solvent film coating. This resulted in a thin coating buildup from sintered dried spray droplets. Although these processes were intended to mimic the effect of a more continuously layed down coating film, the net result was a film with a compromised gloss finish.

In contrast to the above process, the method of the invention utilizes a coating principle which gives preference to laying down continuous wet layers of coating on the tablet surface while maintaining an overall steady state of tablet surface dryness with time averaging. The tablets are alternately flooded with spray and then flash dried by stopping the spray. Repetitive spray cycling allows for the statistical exposure of more tablet surfaces to this treatment, until there is an even distribution of high gloss surfaces throughout the batch. Therefore the coating process of this invention relies on wetting and drying at variable rates as opposed to previous methods which used wetting and drying at constant rates.

This method may be used on tablets which have received a gloss or shine coating by traditional methods using a continuous coating process. Such tablets may be "shined" by using a water spray by the method of the invention. Guidelines for this are shown in Examples 1 and 2. Alternatively, the shine coating may be applied with the method of this invention by using an aqueous coating solution devoid of plasticizers and the method described generally below and used in Example 3. For the most improved gloss, a film coating solution devoid of plasticizers is applied with the method of the invention and then the coated tablet is further water glossed by using the method of the invention to apply a water spray.

METHOD

The method of this invention utilizes an intermittent spraying and drying program whereby tablet surfaces can be momentarily flooded with water, or an aqueous shine coating formulation; and then flash dried to a highly shined finish. The spray flooding requires the use of very high spray rates for a very short period of time. Preferred spray rates are from about 200 grams per minute to about 600 grams per minute per spray gun depending on the size of the equipment. Flash drying requires the maintenance of higher than normal tablet bed temperatures. Normal tablet bed temperatures are commonly between 34 and 37 degrees Centigrade. Preferred tablet bed temperatures for the method of the invention are from 50 to 65 degrees Centigrade.

In practice, the method of this invention requires quite different coating process factor settings from those seen in the FMC manual. Comparisons of the settings required for the process of this invention with those of the FMC manual are shown in Table V.

A major difference is the intermittent character of the spraying step versus continuous spraying used in previous methods. In addition, the spray application rate during the on-spray segment of the intermittent process is about five to about nineteen times the rate of spray application for the continuous process.

A second major difference is the temperature drop between the inlet air temperature and the outlet exhaust air temperature ($\Delta T$) for each process. The preferred temperature drop for the process of this invention is from about 30 to about 70 degrees C.; whereas the suggested temperature drop for the previous continuous method is from about 19 to 24 degrees Centigrade. The temperature drop values for the process of this invention are approximately twice those of the conventional process. In large measure these values characterize each respective drying process. Normal air inlet temperatures for the conventional continuous spray process are about 55 to 58 degrees Centigrade. In comparison, air inlet temperatures for the method of the invention are from about 90 to 130 degrees Centigrade, preferably from about 96 to 127 degrees Centigrade.

The process is aided by keeping the air atomization pressure low in order to produce a coarser spray that will produce the continuous wet layer that is desired. This is in direct contradistinction to the thin coating and sintered spray droplets which is used in the previous continuous spray methods. The revolutions per minute (RPM) of the drying pan are also kept low. The coarser spray and low RPM facilitate production of the desired continuous wet layer In addition, the low RPM allows time for the wetted tablet surfaces to flash dry before there is too much tablet to tablet contact and rubbing produced by the tumbling tablet bed.

COMPOSITION

Although tablets which have been film coated with commonly used film compositions including plasticizers may be shined by the method of the invention by water glossing; the glossing process is aided by the use of gloss coating formulae which are devoid of softening liquid plasticizers. These liquid plasticizers such as polyethylene glycol, propylene glycol and the like, are commonly used in coating formulations, but seem to accentuate the detrimental effects of tablet to tablet rubbing. This rubbing appears to decrease the gloss or shine of the tablet even if an initial "cast film" type of gloss surface was achieved.

Therefore while tablets may be coated with traditional continuous coating techniques using formulae which contain plasticizers and then water glossed, a higher shine will be obtained if the gloss coating formula used, with continuous coating techniques or with intermittent coating techniques described herein, is devoid of plasticizer. The shine coating may be put on as a two step process using water glossing or in a single operation by the method of the invention to achieve a glossy finish.

A preferred aqueous film coating formulation is composed of about 4 to 8% by weight hydroxypropyl methylcellulose (HPMC) and less than about 1% by weight of a combination of sodium hexametaphosphate and lecithin or polyvinylpyrrolidone, most preferably lecithin, dissolved in water to produce an aqueous solution. Most preferred is an aqueous solution containing 6% by weight hydroxypropyl methylcellulose, 0.06% sodium hexametaphosphate and 0.006% lecithin. Obviously, equivalents for these compounds as are well known in the tablet coating art, may be used in approximately the same proportions.

GUIDELINES

The process of this invention requires a number of threshold conditions in order to produce the desired high gloss coating. Since apparently minor adjustments may have a dramatic effect on the degree of gloss obtained, the following guidelines are provided.

If the pan RPM is too fast for a given spray rate to allow continuous wet film formation on the tablet surface, the high gloss effect will not be produced.

If the on-cycle spray rate is too slow for a given pan RPM, the continuous wet layer will not be formed and the high gloss effect will not be produced.

If the spray-on/spray-off time segments are not adjusted properly, the requisite high tablet bed temperature will not be maintained, and flash drying will not occur and the high gloss effect will not be produced.

In summary, the results of coating to produce a high gloss finish depend primarily on two main factors. First, the sprayed material must form a continuous wet film on the tablet surface and, second, the coating process conditions must be adjusted so that the continuous wet film can flash dry into a film that is sufficiently hard that it is not dulled by tablet tumbling.

Given the guidelines above and the specific condition sets shown in the examples, one of skill in the art will be able to achieve a gloss coating using aqueous coating formulations with a variety of conditions and combinations, all of which are contemplated within the scope of the invention. The settings and spray rates given herein are tied to the load of the 24 inch Accela-Cota ® pan. However these settings and rates may be used for larger loads if the number of spray guns is increased.

The following examples disclose preferred embodiments of the invention, but do not limit the applicability of the invention which is solely defined by the claims.

EXAMPLES

EXAMPLE 1

To prepare coated tablets thirteen kilograms (kg) of 5/8 by 9/32 inch capsule-shaped vitamin tablets weighing 615 mg each were placed in a Model 24 inch Accela-Cota ® pan. For convenience, these tablets were aqueously color and clear coated with the method of this invention and the equipment described below in the water glossing section. However, traditional continuous coating techniques may also be used.

The color solution consisted of a dry powder formulation and water. The clear solution is described later. Coating solids resulting in a tablet weight increase of 2.5% for color solids and 0.5% for clear solids were delivered to the tablets. After the clear coating cycle, inspection revealed the tablets were free of defects and were suitable for water glossing.

Water Glossing Coating Equipment

1. Model 24 Accela-Cota ® Pan.
2. Binks Model 61 Spray Gun.
3. Pope Scientific two-gallon capacity S.S. Pressure Vessel for water delivery.
4. Gralab Model 451 Digital Timer plus Quick Exhaust Valves to control spray gun 'on'/spray gun 'off' timing.
0 5. Mettler PE-22 balance for weighing of water delivery.
6. Dickson IR-500 Thermometer for product temperature readings.

While prewarming the tablets to 150° F., the following process parameters were set:
1. 7 rpm Pan Speed.
2. 6 inch Spray Gun to bed spray distance
3. 35 psi Binks spray gun atomizing air pressure.
4. 55 psi Binks spray gun cylinder air pressure.
5. 0.2/4.0 seconds spray gun 'on'/spray gun 'off' time on the Gralab timer.
6. 22.5 psi Pope water delivery pressure vessel air charge. This charge delivered 400 grams of water per minute through the spray gun if sprayed continuously.

At 150° F. product temperature, the following additional parameters were recorded:
1. 260° F. Coating Pan Inlet Temperature
2. 162° F. Coating Pan Exhaust Temperature
3. 3.7 Coating Pan Magnehelic Reading After 10 minutes of water glossing, the following parameters were recorded:
1. 22.5 psi pressure vessel air charge.
2. 19 grams per minute water usage rate.
3. 190 grams cumulative water used.
4. 0.2/4.0 seconds spray gun 'on'/spray gun 'off' gun cycling time.
5. 260° F. inlet temperature.
6. 160° F. exhaust temperature.
7. 144° F. product temperature.
8. 3.8 Coating Pan Magnehelic reading.

Water glossing was stopped after 25 minutes and the tablets were dry cooled to 120° F. Post run observations revealed highly glossy, uniformly shined tablet surfaces. The tablets had a very thin-looking, highly transparent outward tablet surface.

EXAMPLE 2

To prepare coated tablets six kilograms of 11/32 by ¾ inch capsule-shaped vitamin tablets weighing 1295 mg each were placed in a Model 24 Accela-Cota ® pan. To complete the batch loading requirements, nine kilograms of ⅜ inch deep cup round vitamin tablets were added as filler.

These tablets were aqueously color and clear coated using similar equipment, coating solutions and coating techniques as described in Example I. Also, similar coating solids were delivered to the tablets. After the clear coating cycle, inspection revealed the tablets were defect free and suitable for water glossing.

Water Glossing Coating Equipment

1. Model 24 Accela-Cota ® Pan
2. Binks Model 61 Spray Gun.
3. Pope Scientific two-gallon capacity S.S. Pressure Vessel for water delivery.
4. Gralab Model 451 Digital Timer plus Quick Exhaust Valves to control spray gun 'on'/spray gun 'off' timing.
5. Mettler PE-22 balance for weighing of water delivery.
6. Dickson IR-500 Thermometer for product temperature readings.

While prewarming the tablets to 130° F., the following parameters were set:
1. 7 rpm Pan Speed.
2. 6 inch spray gun to bed spray distance.
3. 35 psi Binks spray gun atomizing air pressure.
55 psi Binks spray gun cylinder air pressure.
5. 0.3/2.0 seconds spray gun 'on'/spray gun 'off' time on the Gralab timer.
6. 9.5 psi Pope water delivery pressure vessel air charge. This charge delivered 190 grams of water per minute through the spray gun if sprayed continuously.

At 130° F. product temperature, these additional parameters were recorded:
1. 220° F. Coating Pan Inlet Temperature.
2. 132° F. Coating Pan Exhaust Temperature.
3. 3.6 Coating Pan Magnehelic Reading.
4. 77° F. Ambient Temperature.
5. 21% Ambient RH.

After six minutes of water glossing, the following parameters were recorded:

1. 9.5 psi pressure vessel air charge.
2. 33 grams per minute water usage rate.
3. 200 grams cumulative water used.
4. 0.3/2.0 seconds spray gun 'on'/spray gun 'off' gun cycling time.
5. 220° F. Inlet Temperature.
6. 130° F. Exhaust Temperature.
7. 115° F. Product Temperature.
8. 3.6 Coating Pan Magnehelic Reading.

Water glossing was stopped after 10 minutes and the tablets were dry cooled to 110° F. After run observations revealed highly glossy tablet surfaces.

TABLE I

| MILES MODEL 24 ACCELA-COTA | | | | |
|---|---|---|---|---|
| Process Equipment | | Example 1 | Example 2 | Example 3 |
| Pan | Model 24 Accela-Cota ® | x | x | x |
| Baffle | 4 Straight Bar and 4 Scoop Type | x | x | |
| Baffle | 6 Straight Bar and 2 Scoop Type | | | x |
| Spray Gun | Binks Model 21 | | | x |
| | Binks Model 61 | | | |
| Fluid Cap | 63 S.S. | x | x | x |
| Air Cap | 63 P.B. | x | x | x |
| *Pressure Vessel | Pope Scientific Part #10691 | x | x | x |
| Spray Gun 'on'/'off' timer | Gralab Model 451 | x | x | x |
| Solution Weighing Scales | Mettler PE-22 | x | x | x |
| Product Temperature Thermometer | Dickson IR-500 | x | x | x |

*Pressure vessel is used to deliver coating solution to the spray gun instead of using a pump for that purpose.

TABLE II

| Formulation Ingredients | Multiple Vitamin w/Extra C Example 1 Clear Soln. Grams | Multiple Vitamin Mineral Example 2 Clear Soln. Grams | Multiple Vitamin w/Iron & Calcium Example 3 Clear Soln. Grams |
|---|---|---|---|
| Hydroxypropyl Methylcellulose Powder | 240.00 | 240.00 | 40.00 |
| Lecithin Granules | 0.24 | 0.24 | 0.04 |
| Sodium Hexametaphosphate Pwd. | 2.40 | 2.40 | 0.40 |
| Povidone USP Powder Polyvinylpyrrolidone (PVP) | | | 2.00 |
| D.I. Water | 3757.36 | 3757.36 | 1957.56 |
| TOTAL | 4000.00 | 4000.00 | 2000.00 |
| Total % Solids in Solution: | 6.066 | 6.066 | 2.122 |
| HPMC | Pharmacoat ® Type 603 | | Shinetsu Chemical Company |
| | Methocel ® Type E-3 Premium | | Dow Chemical Company |
| Lecithin | Centrolex ® R | | Central Soya Company |
| Sodium Hexametaphosphate | Vitrafos ® | | Stauffer Chemical Company |
| PVP | Plasdone ® C-15 (K Value 17) | | GAF Corporation |

Procedure for Preparation of Clear Coating Solutions

1. Using a laboratory air mixer as described in Examples 1, 2 and 3; combine all ingredients, except the HPMC powder, in D.I. water for two minutes.
2. When the dry ingredients are wetted, high shear mix with a Silverson Homogenizer as shown in Examples 1 and 3 or a Gifford-Wood Homogenizer as shown in Example 2 for two minutes.
3. Add the HPMC powder and high shear mix for five minutes. Cover container and let stand. When the foam has broken, the solution is ready for subsequent use.

TABLE III

| Clear or Gloss Step Coating Conditions | Multiple Vitamin w/Extra C Tablet Example 1 | Multiple Vitamin Mineral Tablet Example 2 | Multiple Vitamin w/Iron & Calcium Example 3 |
|---|---|---|---|
| Spray Gun to Tablet Bed distance (inches) | 6 | 6 | 5 |
| Spray Rate (gms/min) | 18 | 41–43 | 19 |
| Pressure Vessel Air Charge (psi) | 13 | 4.5 | 52 |
| Air Atomizing (psi) | 40 | 40 | 35 |
| Air Inlet Temperature (°C.) | 121–123 | 104 | 96 |
| Air Exhaust Temperature (°C.) | 59 | 54 | 60 |
| Product Temperature (°F.) | 141–144 | 113 | 125–130 |
| Pan Speed (rpm) | 7 | 7 | 7 |
| Manehelic (Inches Water Column) | 3.6–3.8 | 3.6 | 3.7 |
| Spray Gun 'on' and Spray Gun 'off' timing (seconds) | 0.2/2.5 | 0.4/0.8 | 0.2/5.8 |
| Clear Step Coating Time (minutes) | 60 | 25 | 39 |
| Clear Solution delivered thru gun (grams) | 1070 | 1016 | 747 |

EXAMPLE 3

To prepare coated tablets three kilograms of 11/32 by ⅞ inch capsule-shaped vitamin tablets weighing 1595 mg each were placed in a Model 24 Accela-Cota ® pan. To complete the batch loading requirements, ten kilograms of previously film coated, ⅜ inch deep cup round vitamin tablets were added as filler.

The tablets were aqueously color coated using similar equipment and coating solutions as described in Example I. Also, similar coating solids were delivered to the tablets. After the color coating cycle, inspection revealed the tablets were defect free and suitable for the spraying experiment.

Clear Film Coating Cycle Equipment

1. Model 24 Accela-Cota ® Pan.
2. Binks Model 21 Spray Gun.
3. Pope Scientific two-gallon capacity S.S. Pressure Vessel for water delivery.
4. Gralab Model 451 Digital Timer plus Quick Exhaust Valves to control spray gun "on"/spray gun "off" timing.
5. Mettler PE-22 balance for weighing of solution delivery.
6. Dickson IR-500 Thermometer for product temperature readings.

While prewarming the tablets to 130° F., the following parameters were set:
1. 7 rpm pan speed.
2. 5 inch spray gun to bed spray distance.
3. 35 psi Binks spray gun atomizing air pressure.
4. 55 psi Binks spray gun cylinder air pressure.
5. 0.2/5.8 seconds spray gun "on"/spray gun "off" time on the Gralab timer.
6. 52 psi Pope solution delivery pressure vessel air charge. This charge delivered 600 grams of solution per minute through the spray gun if sprayed continuously.

At 130° F. product temperature, these additional parameters were recorded:
1. 205° F. Coating Pan Inlet Temperature.
2. 3.7 Coating Pan Magnehelic Reading.
3. 82° F. Ambient Temperature.
4. 33% Ambient RH.

After 36 minutes of clear solution spraying, these following parameters were recorded:
1. 52 psi pressure vessel air charge.
2. 19.1 grams per minute solution usage rate.
3. 689 grams cumulative solution used.
4. 0.2/5.8 seconds spray gun "on"/spray gun "off" gun cycling time.
5. 205° F. Inlet Temperature.
6. 142° F. Exhaust Temperature.
7. 125° F. Product Temperature.
8. 3.7 Coating Pan Magnehelic Reading.

Clear solution spraying was stopped after 39 minutes and the tablets were dry cooled to 110° F. After-run observations revealed highly glossy tablet surfaces.

TABLE IV

| Water Glossing Step Conditions | Multiple Vitamin w/Extra C Example 1 | Multiple Vitamin Mineral Example 2 | Multiple Vitamin w/Iron & Calcium Example 3 |
| --- | --- | --- | --- |
| Spray Rate (gms/min) | 19 | 33 | |
| Pressure Vessel air charge (psi) | 22.5 | 9.5 | |
| Air Atomizing (psi) | 35 | 35 | |
| Air Inlet Temperature (°C.) | 127 | 104 | |
| Air Exhaust Temperature (°C.) | 62 | 56 | |
| Product Temperature (°F.) | 144 | 115 | |
| Pan Speed (rpm) | 7 | 7 | |
| Magnehelic (Inches Water Column) | 3.6–3.8 | 3.6 | |
| Spray Gun 'on' and Spray Gun 'off' timing (seconds) | 0.2/4.0 | 0.3/2.0 | |
| Water Glossing Step Coating Time (minutes) | 25 | 10 | |
| Water Delivered thru gun (grams) | 465 | 327 | |

TABLE V

| | Gloss Coating FMC Vitamin Tablets Continuous Spraying | | | Gloss Coating Vitamin Tablets Intermittent Spraying | | | Gloss Coating Process Comparisons | |
| --- | --- | --- | --- | --- | --- | --- | --- | --- |
| | F. 1 | F. 2 | F. 3 | Ex. 1 | Ex. 2 | Ex. 3 | Continuous Spray | Intermittent Spray |
| Air Temp Set (°F.) | 150 | 153 | 153 | — | — | — | 150–153 | |
| Air Atomizing (psi) | 70 | 70 | 70 | 35 | 35 | 35 | 70 | 35 |
| Air Inlet Temp (°C.) | 58–55 | 58 | 56 | 127 | 104 | 96 | 55–58 | 96–127 |
| Air Outlet Temp (°C.) | 35–34 | 34 | 37 | 62 | 56 | 60 | 34–37 | 56–62 |
| ΔT (Air Inlet-Air Outlet) | 22 | 24 | 19 | 65 | 48 | 36 | 19–24 | 36–65 |
| Tablet Bed Temperature (°C.) | — | — | — | 62 | 46 | 52–54 | — | 46–62 |
| Pan (rpm) | 16–17 | 15–16 | 16 | 7 | 7 | 7 | 15–17 | 7 |
| Magnehelic | 4–4.4 | 3.8 | 3.4–3.6 | 3.6–3.8 | 3.6 | 3.7 | no diff. | no diff. |
| Pumping Rate (ml/min) | 40 | 32 | 36–40 | — | — | — | — | — |
| Intermittent Spraying | | | | | | | | |
| Pumping Rate (gm/min) (Spray gun On/Off timing 0.2/4.0) | — | — | — | 19[a] | — | — | 32–40 | 400 |
| Pumping Rate (gm/min) (Spray gun On/Off timing 0.3/2.0) | — | — | — | — | 33[b] | — | 32–40 | 200 |
| Pump Rate (gm/min) (Spray gun On/Off timing 0.2/5.8) | — | — | — | — | — | 19[c] | 43–50 | 600 |
| Total Polishing Time (min.) | 10 | 14 | 14 | 25 | 10 | 39 | 10–14 | 10–39 |
| Continuous Pumping Rate Equivalency (gm/min) with | — | — | — | 400[a] | 200[b] | 600[c] | — | — |

TABLE V-continued

| | Gloss Coating FMC Vitamin Tablets | | | Gloss Coating Vitamin Tablets | | | Gloss Coating Process Comparisons | |
|---|---|---|---|---|---|---|---|---|
| | Continuous Spraying | | | Intermittent Spraying | | | Continuous Spray | Intermittent Spray |
| | F. 1 | F. 2 | F. 3 | Ex. 1 | Ex. 2 | Ex. 3 | | |
| continous spraying | | | | | | | | |

It should be understood that many modifications and variations can be made in the process parameters and coating formulation components used herein without departing from the spirit and scope of the invention, which is solely defined by the claims.

What is claimed is:

1. A method of shining a film coated tablet by water glossing the tablet, comprising:

intermittently spray flooding a bed of film coated tablets in a tablet pan with water by alternating between (a) a spray gun "on" mode in which the tablets are sprayed with water at a rate of between about 200 grams per minute and about 600 grams per minute per spray gun for a period of time sufficient to flood the surfaces of the tablets while rotating the tablet pan at a rate of less than about 10 revolutions per minute and maintaining a tablet bed temperature between about 50° and 65° C., and (b) a spray gun "off" mode in which the tablet pan rotation and tablet bed temperature are maintained and the flooded tablets are dried with air at an inlet air temperature greater than about 90° C. and a temperature drop between the inlet air temperature and exhaust air temperature of from about 30° to 70° C.

2. The method of claim 1 wherein the duration of the spray gun "on" mode is less than 1 second, the duration of the spray gun "off" mode is less than 10 seconds, and the ratio of the duration of the spray gun "on" mode to the duration of the spray gun "off" mode is less than 0.5.

3. The method of producing an aqueous shine coating on tablets, comprising:

coating a bed of the tablets in a tablet pan with a clear aqueous solution which is devoid of plasticizers, which solution consists essentially of about 6% hydroxypropyl methylcellulose, about 0.06% sodium hexametaphosphate and about 0.006% lecithin by weight in water, drying the coated tablets, and intermittently spray flooding the tablets with water by alternating between (a) a spray gun "on" mode in which the tablets are sprayed with water at a rate of between about 200 grams per minute and about 600 grams per minute per spray gun for a period of time sufficient to flood the surfaces of the tablets while rotating the tablet pan at a rate of less than about 10 revolutions per minute and maintaining a tablet bed temperature between about 50° and 65° C., and (b) a spray gun "off" mode in which the tablet pan rotation and tablet bed temperature are maintained and the flooded tablets are dried with air at an inlet air temperature greater than about 90° C. and a temperature drop between the inlet air temperature and exhaust air temperature of from about 30° to 70° C.

* * * * *